(12) United States Patent
Quan et al.

(10) Patent No.: US 9,772,284 B2
(45) Date of Patent: *Sep. 26, 2017

(54) BIOMEDICAL AND CHEMICAL SENSING WITH NANOBEAM PHOTONIC CRYSTAL CAVITIES USING OPTICAL BISTABILITY

(75) Inventors: Qimin Quan, Cambridge, MA (US); Marko Loncar, Belmont, MA (US); Frank Vollmer, Erlangen (DE)

(73) Assignee: President and Fellows of Harvard College, Cambridge, MA (US)

( * ) Notice: Subject to any disclaimer, the term of this patent is extended or adjusted under 35 U.S.C. 154(b) by 773 days.

This patent is subject to a terminal disclaimer.

(21) Appl. No.: 13/641,897

(22) PCT Filed: Apr. 20, 2011

(86) PCT No.: PCT/US2011/033251
§ 371 (c)(1),
(2), (4) Date: Mar. 7, 2013

(87) PCT Pub. No.: WO2011/133670
PCT Pub. Date: Oct. 27, 2011

(65) Prior Publication Data
US 2013/0157882 A1   Jun. 20, 2013

Related U.S. Application Data

(60) Provisional application No. 61/325,854, filed on Apr. 20, 2010.

(51) Int. Cl.
*G01N 21/63* (2006.01)
*G01N 21/77* (2006.01)
(52) U.S. Cl.
CPC ............ *G01N 21/63* (2013.01); *G01N 21/77* (2013.01); *G01N 2021/7789* (2013.01)

(58) Field of Classification Search
None
See application file for complete search history.

(56) References Cited

U.S. PATENT DOCUMENTS 5,166,744 A * 11/1992 Calvani .................. G02F 3/024
356/128
6,493,090 B1  12/2002 Lading et al.
(Continued)

FOREIGN PATENT DOCUMENTS

WO   WO2007/134177   * 11/2007

OTHER PUBLICATIONS

Vollmer, F., D. Braun, et al., "Protein detection by optical shift of a resonant microcavity," Applied Physics Letters 80(21): 3 (2002).
(Continued)

*Primary Examiner* — Melanie Y Brown
(74) *Attorney, Agent, or Firm* — Peter A. Nieves; Sheehan Phinney Bass & Green PA (57) ABSTRACT

A miniature optical biosensor and biosensor array where high sensitivity for detection of biomolecular interaction does not require a fluorescent label. Non-linear frequency-shifts of optical resonators ('nanobeams') provide a digital all-or-nothing response to equilibrium binding of a biomarker to surface-immobilized bio-recognition elements, a signal suitable to identify active components in genetic and proteomic circuits, as well as toxic substances. The threshold level for the digital response is adjustable to accommodate for varying receptor affinities. A bistable cavity sensing (BCS) method can be used to track the shift of the resonance induced by the analyte more precisely than the conventional cavity sensing method, where the resolution is limited by the cavity linewidth. BCS method can be used to quantitate the concentration of the analyte, and their binding kinetics, affinities and etc.

16 Claims, 9 Drawing Sheets

(56) References Cited

U.S. PATENT DOCUMENTS

| | | | |
|---|---|---|---|
| 7,778,296 B1* | 8/2010 | Vuckovic | B82Y 20/00 372/41 |
| 2002/0097401 A1* | 7/2002 | Maleki et al. | 356/436 |
| 2004/0150818 A1* | 8/2004 | Armstrong | B82Y 10/00 356/301 |
| 2005/0078731 A1* | 4/2005 | Fan | G01N 21/7746 372/94 |
| 2005/0281298 A1 | 12/2005 | Kupershmidt | |
| 2006/0062507 A1* | 3/2006 | Yanik | B82Y 20/00 385/5 |
| 2006/0062508 A1* | 3/2006 | Guo et al. | 385/12 |
| 2006/0188398 A1* | 8/2006 | Yano et al. | 422/82.01 |
| 2006/0227331 A1* | 10/2006 | Vollmer et al. | 356/483 |
| 2007/0076201 A1 | 4/2007 | Babin | |
| 2008/0212068 A1 | 9/2008 | Sailor et al. | |
| 2008/0219615 A1* | 9/2008 | Cunningham | B01L 3/5085 385/12 |
| 2009/0045317 A1* | 2/2009 | Fushman | B82Y 20/00 250/201.1 |
| 2009/0136181 A1 | 5/2009 | Vollmer et al. | |
| 2009/0305230 A1* | 12/2009 | Beattie | G01N 21/77 435/5 |
| 2010/0028898 A1* | 2/2010 | Aoki | G01N 21/6452 435/6.12 |
| 2010/0243448 A1* | 9/2010 | Maurer et al. | 204/450 |
| 2010/0248391 A1* | 9/2010 | Garcia Tello | 436/501 |
| 2011/0019186 A1* | 1/2011 | Himmelhaus et al. | 356/317 |
| 2011/0028346 A1* | 2/2011 | Chakravarty | G01N 21/253 506/12 |

OTHER PUBLICATIONS

Arnold, S., M. Khoshsima, et al., "Shift of whispering-gallery modes in microspheres by protein adsorption," Optics Letters 28(4): 3 (2003).

Teraoka, I., S. Arnold, et al., "Perturbation approach to resonance shifts of whispering-gallery modes in a dielectric microsphere as a probe of a surrounding medium," Journal of the Optical Society of America B-Optical Physics 20(9): 1937-1946 (2003).

Vollmer, F., S. Arnold, et al., "Multiplexed DNA quantification by spectroscopic shift of two microsphere cavities," Biophysical Journal 85(3): 6 (2003).

Vollmer, F., S. Arnold, et al., "Single Virus Detection from the Reactive Shift of a Whispering-Gallery Mode," Proc. Nat'l Acad. Sci. U. S. A. 105(52): 5 (2008).

Vollmer, F. and P. Fischer, "Ring-resonator-based frequency-domain optical activity measurements of a chiral liquid," Optics Letters 31(4): 453-455 (2006).

Loncar, M., B. G. Lee, et al., "Design and fabrication of photonic crystal quantum cascade lasers for optofluidics," Optics Express 15(8): 4499-4514 (2007).

Loncar, M., A.Scherer, et al., "Photonic crystal laser sources for chemical detection," Applied Physics Letters 82: 4648 (2003).

MacBeath, G., "Protein microarrays and proteomics," Nature Genetics 32: 526-532 (2002).

Zhu, H. and M. Snyder, "Protein chip technology," Current Opinion in Chemical Biology 7(1): 55-63 (2003).

Marshall, A. and J. Hodgson, "DNA chips: An array of possibilities," Nature Biotechnology 16(1): 27-31 (1998).

Schena, M., R. A. Heller, et al., "Microarrays: biotechnology's discovery platform for functional genomics," Trends in Biotechnology 16(7): 301-306 (1998).

Jaklevic, J. M., H. R. Garner, et al., "Instrumentation for the genome projtect," Annual Review of Biomedical Engineering 1: 649-678 (1999).

Nuwaysir, E. F., M. Bittner, et al., "Microarrays and toxicology: The advent of toxicogenomics," Molecular Carcinogenesis 24(3): 153-159 (1999).

Heller, M. J., "DNA microarray technology: Devices, systems, and applications," Annual Review of Biomedical Engineering 4: 129-153 (2002).

Santacroce, R., A. Ratti, et al., "Analysis of clinically relevant single-nucleotide polymorphisms by use of microelectronic array technology," Clinical Chemistry 48(12): 2124-2130 (2002).

Simon, R., M. D. Radmacher, et al., "Pitfalls in the use of DNA microarray data for diagnostic and prognostic classification," Journal of the National Cancer Institute 95(1): 14-18 (2003).

Smyth, G. K. And T. Speed, "Normalization of cDNA microarray data," Methods 31(4): 265-273 (2003).

Yanaihara, N., N. Caplen, et al., "Unique microRNA molecular profiles in lung cancer diagnosis and prognosis," Cancer Cell 9(3): 189-198 (2006).

Ramsay, G., "DNA chips: State-of-the-art," Nature Biotechnology 16(1): 40-44 (1998).

Zhu, H., M. Bilgin, et al., "Global analysis of protein activities using proteome chips," Science 293(5537) dated Sep. 2001.

* cited by examiner

BIOMEDICAL AND CHEMICAL SENSING WITH NANOBEAM PHOTONIC CRYSTAL CAVITIES USING OPTICAL BISTABILITY

CROSS-REFERENCE TO RELATED APPLICATIONS

The present application claims the benefit of the filing date of U.S. Provisional Application Ser. No. 61/325,854 entitled "Digital Biosensing with Nanobeam Photonic Crystal Cavities" and filed on Apr. 20, 2010.

The above cross-referenced related application is hereby incorporated by reference herein in its entirety.

STATEMENT REGARDING FEDERALLY SPONSORED RESEARCH OR DEVELOPMENT

Not applicable.

BACKGROUND OF THE INVENTION

Field of the Invention

The present invention relates to optical resonators and, more specifically, to biomedical and chemical sensing using optical resonators.

Brief Description of the Related Art

Resonators play a very important role in RF (radio frequency), microwave and electronic systems and are poised to play an equally important role in optics and photonics. Recently, it has been shown that optical resonators are particularly sensitive for detection of chemicals, biochemicals and virus nanoparticles. See, for example, Vollmer, F., D. Braun, et al., "Protein detection by optical shift of a resonant microcavity," *Applied Physics Letters* 80(21): 3 (2002); Arnold, S., M. Khoshsima, et al., "Shift of whispering-gallery modes in microspheres by protein adsorption," *Optics Letters* 28(4): 3 (2003); Teraoka, I., S. Arnold, et al., "Perturbation approach to resonance shifts of whispering-gallery modes in a dielectric microsphere as a probe of a surrounding medium," *Journal of the Optical Society of America B-Optical Physics* 20(9): 1937-1946 (2003); Vollmer, F., S. Arnold, et al., "Multiplexed DNA quantification by spectroscopic shift of two microsphere cavities," *Biophysical Journal* 85(3): 6 (2003); and Vollmer, F., S. Arnold, et al., "Single Virus Detection from the Reactive Shift of a Whispering-Gallery Mode," *Proc. Nat'l Acad. Sci. U.S.A.* 105(52): 5 (2008). The detection principle is based on the exposure of the resonator (cavity) to the sample. This can be achieved either by directly introducing the sample in the optical cavity (Vollmer, F. and P. Fischer, "Ring-resonator-based frequency-domain optical activity measurements of a chiral liquid," *Optics Letters* 31(4): 453-455 (2006) and Loncar, M., B. G. Lee, et al., "Design and fabrication of photonic crystal quantum cascade lasers for optofluidics," *Optics Express* 15(8): 4499-4514 (2007)), or alternatively by adsorbing the chemical to the cavity boundary (surface)(see, Vollmer, F., D. Braun, et al., "Protein detection by optical shift of a resonant microcavity," *Applied Physics Letters* 80(21): 3 (2002)) or, as a third alternative, by immersing the cavity in a bulk sample (see, Teraoka, I., S. Arnold, et al., "Perturbation approach to resonance shifts of whispering-gallery modes in a dielectric microsphere as a probe of a surrounding medium," *Journal of the Optical Society of America B-Optical Physics* 20(9): 1937-1946 (2003) and Loncar, M., A. Scherer, et al., "Photonic crystal laser sources for chemical detection," *Applied Physics Letters* 82: 4648(2003)). The presence of the sample, quantity and optical properties can be determined from a change of one or more characteristic resonator parameters such as resonance wavelength and intensity.

Also, it recently has been shown that optical resonators can be defined in 1D photonic crystal type resonators. The photonic crystal platform enables strong localization of photons to sub-wavelength volumes for long periods of time, provides means to control optical signals at single-photon level. This progress in nanophotonics has been paralleled with progress in the field of nanoscale electro-mechanical systems (NEMS) and realization of ultra-sensitive mass sensors capable of detecting single-molecules.

The present invention relates to the broader field of high-throughput (HT) biosensing, i.e. the detection and characterization of biological material for toxicology, genomics and proteomics. With genomes of many species completed, a revolution in genetic and proteomic analysis has begun. Technological advances of recent years have made this revolution possible by replacing labor-intensive, traditional biochemical methods with automated nucleic acid and protein analysis techniques. See, for example, Marshall, A. and J. Hodgson, "DNA chips: An array of possibilities," *Nature Biotechnology* 16(1): 27-31 (1998); Schena, M., R. A. Heller, et al., "Microarrays: biotechnology's discovery platform for functional genomics," *Trends in Biotechnology* 16(7): 301-306 (1998); Jaklevic, J. M., H. R. Garner, et al., "Instrumentation for the genome project," *Annual Review of Biomedical Engineering* 1: 649-678 (1999); and Nuwaysir, E. F., M. Bittner, et al., "Microarrays and toxicology: The advent of toxicogenomics," *Molecular Carcinogenesis* 24(3): 153-159 (1999). To exploit the vast amount of genetic and proteomic information for medical diagnostic purposes, drug discovery, food testing, forensic sciences, and environmental monitoring, it is necessary to further miniaturize and integrate DNA/RNA and protein analysis techniques into robust and easy to manufacture lab-on-a-chip and micro total analysis systems. See, Heller, M. J., "DNA microarray technology: Devices, systems, and applications," *Annual Review of Biomedical Engineering* 4: 129-153 (2002); Santacroce, R., A. Ratti, et al., "Analysis of clinically relevant single-nucleotide polymorphisms by use of microelectronic array technology," *Clinical Chemistry* 48(12): 2124-2130 (2002); Simon, R., M. D. Radmacher, et al., "Pitfalls in the use of DNA microarray data for diagnostic and prognostic classification," *Journal of the National Cancer Institute* 95(1): 14-18 (2003); Smyth, G. K. and T. Speed, "Normalization of cDNA microarray data," *Methods* 31(4): 265-273 (2003); and Yanaihara, N., N. Caplen, et al., "Unique microRNA molecular profiles in lung cancer diagnosis and prognosis," *Cancer Cell* 9(3): 189-198 (2006). Gene chips provide such a means for high-throughput DNA screening using oligonucleotide arrays.

Commercially available protein- and gene 'chips' quantitate the fluorescence intensity of labeled biomarkers after binding to specific recognition elements that were previously immobilized ('spotted') on a chip substrate. See, Ramsay, G., "DNA chips: State-of-the-art," *Nature Biotechnology* 16(1): 40-44 (1998); Zhu, H., M. Bilgin, et al., "Global analysis of protein activities using proteome chips," *Science* 293(5537): 2101-2105 (2001); MacBeath, G., "Protein microarrays and proteomics," *Nature Genetics* 32: 526-532 (2002); and Zhu, H. and M. Snyder, "Protein chip technology," *Current Opinion in Chemical Biology* 7(1): 55-63 (2003). The equilibrium intensity of the bound fluorescent biomarker is then compared to a threshold level to decide if an associated gene is either active or silent (Schena, Shalon et al. 1995). There are several major problems associated with this label-based detection scheme: First, it is often challenging to detect fluorescently labeled molecules against the background of excess fluorophore which can never be completely removed after chemical labeling. Second, the threshold for detection cannot be adjusted to accommodate for varying receptor affinities. Third, the need for target amplification and labeling can directly interfere with the analysis: amplification and labeling can change the original concentration of biomarkers, may not be practical for certain proteins or nucleic acids, and is an impediment for further automation of HT approaches in fully automated point-of-care testing (POCT) applications. And lastly, acquisition and analysis of the fluorescent image of the microarray is technically involved and limits the use of the DNA chip technology as the analytic part of a small, portable, and robust lab-on-a-chip device.

SUMMARY OF THE INVENTION

In a preferred embodiment, the present invention is a label-free optical biosensing method based on optical resonator detection technology with the following advantages: 1) rapid 'digital' (all-or-nothing) read-out without the need for labeling; 2) quantitative analysis of the concentration of analytes without the need for labeling; 3) planar microfabricated platform in a silicon material system; 4) applicable for detection of virtually any biomarker; 5) scalable in array-format and amenable to mass-production and commercialization such that it can be distributed to the members of biology and medical communities. These device parameters are achieved by using a photonic crystal 'nanobeam' resonator as the optical sensing element. See, Quan, Q., P. B. Deotare, et al., "Photonic Crystal Nanobeam Cavity Strongly Coupled to the Feeding Waveguide," *Applied Physics Letters*, 96, 203102 (2010). The biosensing architecture can be utilize for realization of multiplexed, highly-sensitive and inexpensive threshold-level detection systems for HT applications in genomics and proteomics, as well as for applications in biomedicine, forensics, toxicology, environmental monitoring and homeland-security.

In a preferred embodiment, the present invention is an optical device. The devices is comprised of a laser source, input waveguides connected to the laser, a material structured on the micro- or nanoscale to localize light in a modal volume where constructive interference produces optical resonance, wherein the material exhibits third-order nonlinearity and is modified with molecular recognition elements immobilized within some part of the optical field, the material being connected to the input waveguides, output waveguides connected to the material and a photo-detector connected to the output waveguides. The material is exposed on one or more sides to a liquid sample in a sample volume. A geometry of the micro- or nanoscale structure may be a geometry that produces an optical cavity structure. Exemplary geometries of the micro- or nanoscale structure of the material are the following: a photonic crystal defect cavity, a photonic crystal nanobeam cavity, a photonic crystal, a ring resonator, a fabry-perot cavity, and a spherical whispering gallery mode resonator. The material may be, for example, silicon, silica, silicon nitrate, diamond, doped glass, high-index glass, quartz, polymer, polydimethylsiloxane, InP, or III-V materials. The non-linearity of the material may originate from heating of the material by two-photon and/or free carrier absorption. Further, the non-linearity of the material originates from second order nonlinearity, opto-mechanically induced nonlinearity, and Kerr nonlinearity. A resonant frequency of the device may be, for example, in the visible, in the near-infrared, in the mid-infrared or in the UV. A resonant frequency of each cavity can be reconfigured mechanically, by heating, by carrier injection, or by nonlinear optical processes. Each micro-cavity may be individually excited, or simultaneously excited, where the micro-cavities are excited using optical fibers, tapered optical fibers, or through focused or non-focused optical beams. A signal from each micro-cavity is transferred to optical waveguides, arrays of optical fibers, imaging arrays, or detector arrays. The sample volume comprises a microfluidic channel, an open reservoir, or a capillary. Several cavities may be multiplexed in array or matrix format on a chip substrate. The molecular recognition elements may be comprised of one of the following: DNA, single stranded DNA, proteins, antibodies, dendrimers, nanostructures, bacterial S proteins, lectins, glycoproteins, membranes, membrane components, lipid bilayers, and organelles.

In another embodiment, the present invention is a method for detection of biomolecular targets. The method comprises the steps of coupling of light to a device at an optical frequency that is slightly blue-detuned from the resonance frequency, detecting transmitted power with the photodetector, exposing the molecular recognition elements to target molecules dissolved in the liquid sample, recording a discrete change of transmitted power in response to specific binding of target molecules to the recognition elements, recording a power vs. time trace on a computer and resetting the device by blue-detuning so that the new frequency is blue-detuned to the new resonance frequency of the device, where the devices is comprised of a laser source, input waveguides connected to the laser, a material structured on the micro- or nanoscale to localize light in a modal volume where constructive interference produces optical resonance, wherein the material exhibits third-order nonlinearity and is modified with molecular recognition elements immobilized within some part of the optical field, the material being connected to the input waveguides, output waveguides connected to the material and a photo-detector connected to the output waveguides.

In another embodiment, the present invention is a method of analyzing the concentration, binding kinetics and affinity of biomolecular targets. The method comprises the steps of coupling of light to the device at various optical frequencies, detecting a transmitted power with the photodetector at each frequency and analyzing a resonance obtained by the photodetector, where the devices is comprised of a laser source, input waveguides connected to the laser, a material structured on the micro- or nanoscale to localize light in a modal volume where constructive interference produces optical resonance, wherein the material exhibits third-order nonlinearity and is modified with molecular recognition elements immobilized within some part of the optical field, the material being connected to the input waveguides, output waveguides connected to the material and a photo-detector connected to the output waveguides.

In still another embodiment, the present invention is a method to accommodate for varying receptor affinity by blue detuning of the resonance frequency to a certain wavelength so that a certain number of molecules will trigger a discrete change in transmitted optical power.

In still another embodiment, the present invention is a method to achieve high throughput and parallel detection by multiplexing cavities in an array or matrix format on the chip. Each cavity can be coupled through waveguide using optical fibers, or alternatively can be excited from top using scattering methods, or alternatively through grating couplers. The signals from each cavity can be individually collected by optical fibers with a detector, or alternatively can be collected by a CCD camera or imaging array that is capped on top of the device.

Still other aspects, features, and advantages of the present invention are readily apparent from the following detailed description, simply by illustrating preferable embodiments and implementations. The present invention is also capable of other and different embodiments and its several details can be modified in various obvious respects, all without departing from the spirit and scope of the present invention. Accordingly, the drawings and descriptions are to be regarded as illustrative in nature, and not as restrictive. Additional objects and advantages of the invention will be set forth in part in the description which follows and in part will be obvious from the description, or may be learned by practice of the invention.

BRIEF DESCRIPTION OF THE DRAWINGS

FIGS. 1A-1D illustrate a refractive-index sensor based on photonic crystal cavities in accordance with a preferred embodiment of the present invention.

FIG. 2C-1 is a graph illustrating that a binding curve is recorded by tracking the minimum corresponding to the wavelength shift $\Delta\lambda$. See, Vollmer et al., *Nature Methods* 2008; 4:591.

FIG. 2C-2 is a blow-up of a portion of FIG. 2C-1.

FIG. 5B is a graph of power in -power out relation in the presence of optical bistablity. The system exhibits nonlinear, bistable, behavior when a detuning $\delta > 3^{1/2}\gamma_0$, where $\gamma_0$ is linewidth of the cavity resonance ($\gamma_0 = \omega_0/Q$, $\omega_0 = 2\pi c_0/\lambda$, $\lambda$ is resonant wavelength). The wavelength is normalized by the resonance wavelength (without nonlinearity), and input and output powers are normalized by the characteristic power $P_0$.

DETAILED DESCRIPTION OF THE PREFERRED EMBODIMENTS

Figure 1A:
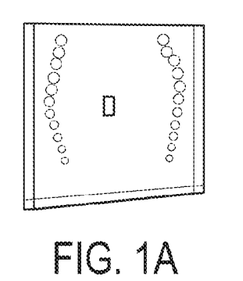
FIG. 1A is a diagram of a PDMS microfluidic chip with photonics chip embedded in the middle.
Figure 1B:
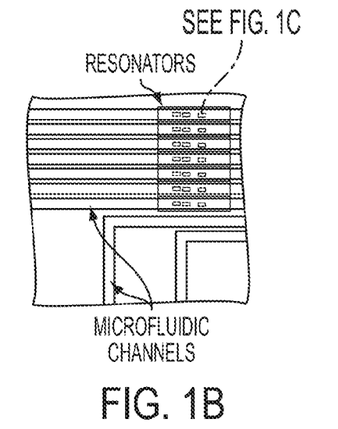
FIG. 1B is a blow-up showing microfluidic channels aligned onto optical resonators shown in FIG. 1C.
Figure 1C:
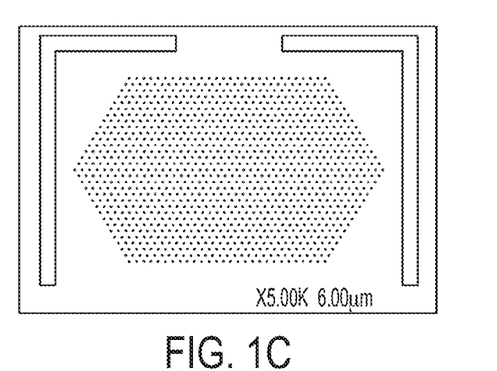
Figure 1D:
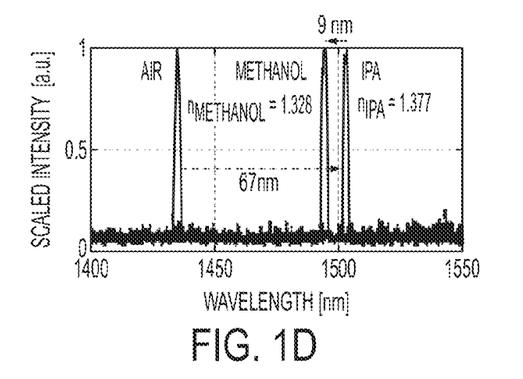
FIG. 1D is a sensing graph showing cavity resonance shifts when channels are filled with fluids.
Figure 3A:
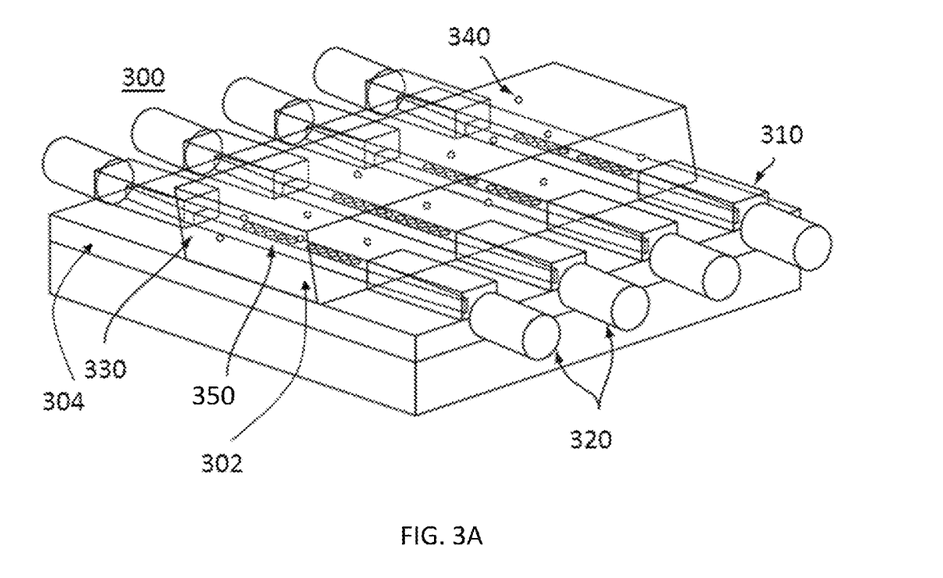
FIG. 3A is a perspective view of a sensing platform in accordance with a preferred embodiment of the present invention.
Figure 3B:
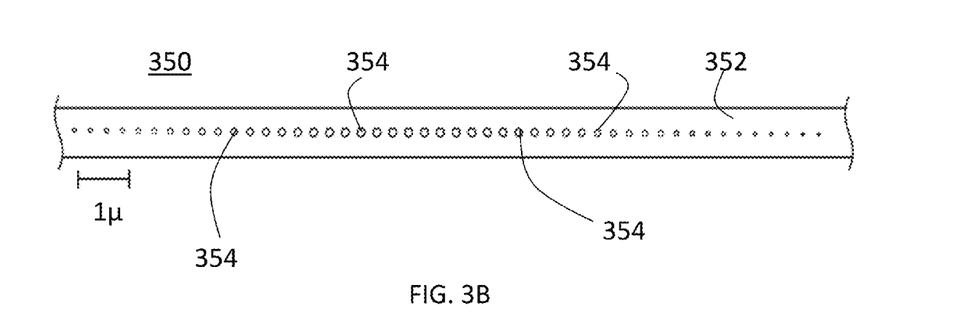
FIG. 3B is a SEM micrograph of a cavity in accordance with a preferred embodiment of the present invention.

A preferred embodiment of the present invention is a nanophotonic platform based on optical waveguides and high-quality factor ($Q \sim 10^5$) non-linear photonic crystal cavities (for example, FIG. 3) capable of multiplexed, highly-sensitive both threshold-level detection and quantitative analysis of the binding of bio-molecules to immobilized recognition elements. This highly-sensitivity approach not only obviates the need for target labeling and introduces microfluidics-based sample delivery, but also enhances the specificity and sensitivity of previous photonic crystal-based detection schemes that were based on measuring the change of the refractive index induced by a bulk analyte (FIG. 1D).

In the past, a technique for the real-time label-free analysis of biomolecules that uses high-quality optical resonances in microsphere sensors ~50-200 µm in diameter has been introduced. See, Vollmer, F., S. Arnold, et al., "Novel, fiber-optic biosensor based on morphology dependent resonances in dielectric micro-spheres," *Biophysical Journal* 82(1): 789 (2002); Vollmer, F., D. Braun, et al., "Protein detection by optical shift of a resonant microcavity." *Applied Physics Letters* 80(21): 3 (2002); and Vollmer, F., S. Arnold, et al., "Single Virus Detection from the Reactive Shift of a Whispering-Gallery Mode." *Proc Natl Acad Sci USA* 105 (52): 5 (2008). This method enables the quantitative analysis, with an unprecedented sensitivity, of molecular properties such as concentration, binding kinetics and affinity. Although the sensitivity of the microbead biosensors has been shown to routinely surpass the sensitivity limit set by other commercial label-free techniques such as surface plasmon resonance sensors (SPR), the microbead-based biosensor faces important challenges with further chip-scale integration: each microbead has to be coupled to an optical fiber, which makes it difficult to produce larger arrays of biosensing elements and which is an impediment to mass-production. Furthermore, this technique has almost reached its sensitivity limit. The present invention has the potential of replacing the microsphere sensing element with a photonic crystal nanobeam resonator. The planar resonator geometry can be more easily fabricated in array format and integrated with microfluidics. Furthermore, a novel sensing modality is disclosed that exploits non-linear light interaction for threshold-level detection and quantitative analysis in toxicology, gene- and protein chip applications Silicon-on-insulator (SOI) is a particular appealing materials system to reach this goal. In addition to being the material of choice for the microelectronics industry, silicon is an excellent optical material that is suitable for the realization of optical resonators with ultra-high quality factor and large optical bistability. Moreover, the SOI platform enables integration of photonic devices side-by-side with microelectronic devices, thus enabling hybrid circuits with additional functionality. It is important to note that largescale manufacturing of our devices can capitalize on advances in the silicon microelectronics and telecom industries, facilitating inexpensive manufacturing of the proposed sensing platform.

The specific innovations of the present biosensor design can be summarized as follows:
  Novel sensing technique based on threshold-level detection using optical bistability for DNA hybridization, proteomics and toxicology.
  Quantitative analysis of biomarker concentration with ultrahigh sensitivity enhanced by optical bistability, named as bistable cavity sensing (BCS) method.
  Photonic crystal nanobeam cavity designs, with built in optical nonlinearity, for biosensing applications. Integration between nanophotonics and microfluidics for chip-scale biosensing. Specificity for detection through the immobilization of recognition elements on the cavity surface.
Fabrication and Application of Nanobeam Sensors in an Array Format for DNA and Protein Detection, Sensor Integration and Multiplexing. Surface Modification of Large Sensor Arrays for Detection of Several Biomarkers in Parallel The use of a photonic-crystal-based micro-resonator instead of glass microspheres for biosensing applications has several advantages: The planar nanobeam geometry can be fabricated in array format, where coupling waveguide and microcavity are integrated on the same planar SOI wafer. Furthermore, the sensitivity for biosensing will be greatly enhanced due to the very small modal volume of the photonic crystal-based microcavity, as shown in Table 1.

TABLE 1

Comparison of microsphere and nanobeam cavities

| Cavity type | Microsphere | Nanobeam |
|---|---|---|
| Material | Silica | Silicon |
| Modal volume | >200 μm$^3$ | <1 μm$^3$ |
| Thermo-optic | $1 \times 10^{-5}$ K$^{-1}$ | $1.85 \times 10^{-4}$ K$^{-1}$ |
| Thermal conductivity | 1.38 W m$^{-1}$ K$^{-1}$ | 149 W m$^{-1}$ K$^{-1}$ |

In addition, the thermo-optic coefficient for silicon is much higher as compared to glass, which allows us to exploit thermal non-linear effects (optical bistability) to increase the signal to noise ratio (SNR) as well as the sensitivity in biosensing applications.

Digital biosensing exploits optical bistability in microresonators to realize threshold-level detection at unprecedented sensitivity levels, possibly down to single molecules. The approach is described in greater detail in the following. In short, large cavity Q results in build-up of significant optical power in very small cavity volume which results in the optical bistability of the cavity induced by thermo-optic effect. The bifurcation the optical bistability will produce a signal with high SNR (signal-to-noise ratio) when the biomarkers are beyond a certain threshold. Large thermal resistance of nanobeam cavity makes it ideally suited for this application. In addition, encapsulating the nanobeam cavity into a perfluoropolymer layer like CYTOP (Anolick, Hrivnak et al. 1998; Mikes, Yang et al. 2005; Okamoto and Teng 2009) (e.g. by spin-coating) further thermally isolates the cavity. Moreover, CYTOP layer protects the cavity from the analyte that is delivered via microfluidic channel on top of the cavity.

With a tunable laser, the concentration of the biomarker can also be analyzed by monitoring the shift of the nonlinear resonance before and after the binding of biomarkers. Instead of tracking the resonance peak of the Lorentzian resonance, the bifurcation point of the nonlinear spectrum is tracked. As will be introduced in more detail, this sensing method may be called bistable cavity sensing (BCS). This method will break the fundamental resolution limit in tracking the Lorentzian peak.

The recently demonstrated high quality factor (Q=750, 000) of photonic crystal nanobeam cavities (Deotare, McCutcheon et al. 2009) are on par with those found in much larger cavity geometries. The quality factor of a cavity is a measure of its ability to trap photons. Therefore, the optical power that is trapped inside a high-Q cavity can be several orders of magnitude larger than the power coupled into the cavity, facilitating the interaction between molecules and light resulting in increased sensitivity. The near-field of the nanobeam cavity needed for this interaction is highly "accessible", that is the overlap between the cavity field and analyte is enhanced, which is ideally suited for bio-sensing applications. Nanobeam cavities also have an ultra-small footprint, exactly the same as that of optical waveguide and 10-20 times smaller than that of other dielectric-based resonators—nanobeams are the smallest resonant structures that can be made with dielectrics only. Therefore, these cavities are ideal candidates for realization of highly-integrated biosensing platform.

A planar silicon-based photonic crystal nanobeam cavity which can be fabricated in array format and integrated with microfluidic superstructures may be used to realize HT label-free detection in a gene or protein chip format. In addition, the greatly reduced modal volume of the nanobeam cavity (Table 1) in combination with the larger thermo-optic coefficient allows access to non-linear thermo-optic behavior at micro-to nano-watt power levels which may be used to increase sensitivity for threshold-level ('digital') molecular detection and the BCS method. Furthermore, the planar geometry can be easily integrated with microfluidics and other photonic components, and is ultimately amenable to mass-production by deep UV photolithography.

Digital Bio-Sensing Based on Optical Bistability: Proposal and Theoretical Foundations High-Q whispering-gallery-mode (WGM) optical cavities have been experimentally demonstrated as an excellent candidate for label-free and passive detection. The sensitivity of this cavity resonance-based detection scheme, however, is limited by the linewidth of the cavity, i.e. spectrally limited. Further pushing this limit would require higher cavity Q or smaller mode volume, which would be challenging since Q of WGM microcavities have reached the limit of material loss. The present invention uses a novel mechanism that allows a noise-limited sensitivity by utilizing the cavity enhanced optical bistability effects. The sensing mechanism is based on a third-order optical nonlinearity and works conceptually as follows: (i) light from a semiconductor laser is coupled into the optical cavity. The cavity resonance is purposely (slightly) blue-detuned from the laser's wavelength, resulting in low transmitted signal through the cavity; (ii) molecules of interest that bind to the cavity surface and change the cavity resonance, pushing it towards the laser's wavelength; (iii) this results in more light being coupled into the cavity, which heats up the silicon cavity, via two-photon absorption and free-carrier absorption effects, producing an additional wavelength shift owing to the thermal dependence of silicon's refractive index, dn/dT. (iv) this additional wavelength shift now tunes the cavity exactly on resonance with the incoming laser beam, resulting in large transmitted signal through the cavity. The sensitivity of this approach, that is the minimal number of bio-molecules that are needed to 'switch' the cavity on resonance, is determined by the initial cavity detuning.

The smallest number and/or size of bound molecules that can trigger our optical switch is limited only by noise of the system that can prematurely trigger the bistable optical response, including the instrumentation noise (i. e. wavelength and Poynting stability) and Brownian motion of the analyte in the vicinity of the microcavity. Assuming a realistic stability noise, limited by power fluctuation of the diode laser on the order of 5-10%, and a cavity Q~100 000, an ultimate sensitivity is estimated to be single particles in the 5-10 nm size range, comparable to the size of a large macromolecule such as a ribosome. Further enhancement in sensitivity down to single bovine serum albumin molecules (BSA) can be achieved by further stabilizing the laser source and eliminating other sources of instrument noise. This ultimate level of detection has the potential to surpass that of highly-sensitive label based techniques such as enzyme-linked immunosorbent assays (ELISA) and that of other state-of-the-art label-free optical techniques such as surface plasmon, by several orders of magnitude. A number of cavities can be used in parallel, each with different detuning from the incoming laser light. This allows accommodating for varying receptor affinities when using this approach in sensor arrays for HT applications.

Figure 5A:
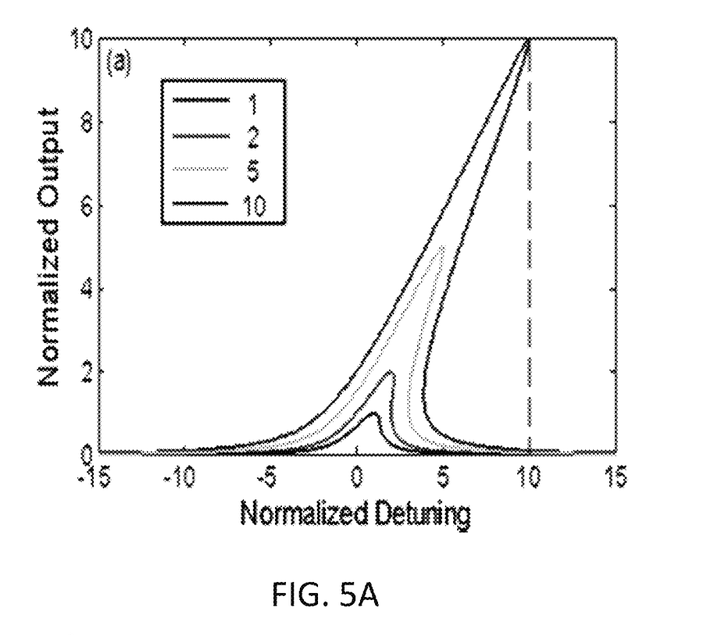
FIG. 5A is a graph of calculated cavity resonance for different laser power levels in uW.

The detailed theory of digital biosensing is outlined below. For a cavity with Kerr nonlinearity, in the steady state, the input and output power satisfies $$\frac{P_{out}}{P_{in}} = \frac{Q_{total}^2/Q_{wg}^2}{1+(P_{out}/P_0 - 2(\lambda - \lambda_0)/\gamma_0)},$$

where $Q_{total}$ is the total quality factor of the cavity and $Q_{wg}$ is the coupling Q factor to the feeding waveguide, $\gamma_0$ is the natural linewidth of the "cold" cavity (without non-linearity, e.g. $\chi^{(3)}=0$). The characteristic optical power is defined as $P_0=3\kappa Q_{total}Q_{wg}(\omega/2nc)^2\chi^{(3)}$, where $\kappa$ is the nonlinear feedback parameter introduced by Soljacic et. al, and where $\kappa\sim1/V$ (V is cavity mode volume) is an indicator of the extent of the field that is confined in the nonlinear region. See, Soljacic, M., C. Luo, et al., "Nonlinear photonic crystal microdevices for optical integration," *Optics Letters* 28(8): 637-639 (2003). FIG. 5A shows theoretically predicted output (transmitted) power spectrum for various input power levels. A positive value of $\chi^{(3)}$ results in the optical bistability, evidenced by the 'titled' Lorentzian line-shape (red detuning is assumed).

Figure 5B:
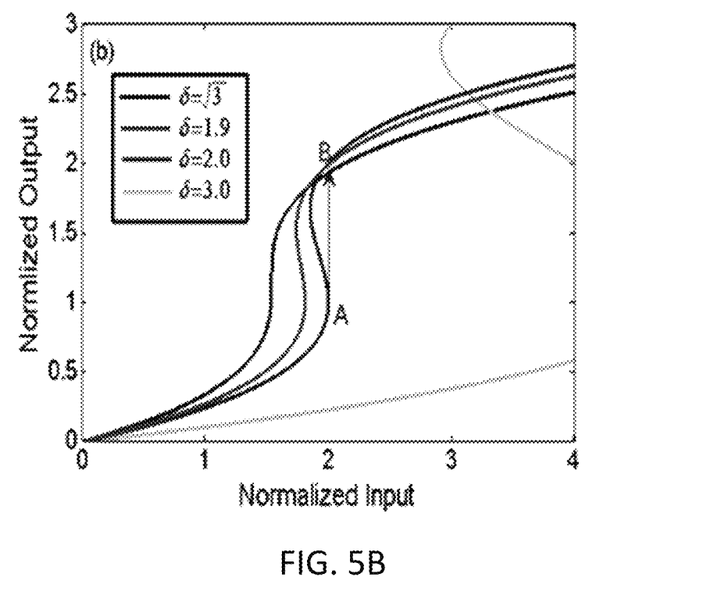
Figure 6:
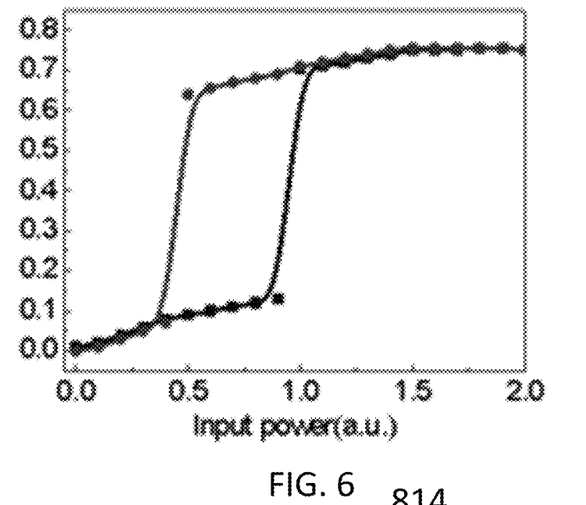
FIG. 6 is a graph of experimental results showing $P_{out}$ as a function of $P_{input}$. Optical bistability can be seen.

FIG. 5B shows the output vs. input power at different detunings $\delta=\lambda-\lambda_0$ normalized to cavity linewidth $\gamma_0$. A digital sensing mechanism can be illustrated in following way: (i) the system is initialized in state A on the blue curve; (ii) the arrival of analyte results in a red-shift of the cavity resonance (since the analyte has higher index than carrying fluid, e.g. water), resulting in smaller detuning $\delta$ so that now more power is coupled to the cavity and normalized input $P/P_0$ increases. The consequence of this is that the system jumps from one curve (point A) to the other curve (point B); and (iii) this results in the stark change of the power transmitted through the cavity which can be easily detected. Interestingly, even after the analyte leaves the cavity region, the system remains in the state B (high transmission state). That is, due to optical bistability, the system has a built in memory and remembers if analyte was present or not. Therefore, this detection scheme may be referred to as "digital sensing." After the read-out phase is over, the system can be brought back to initial state A, and prepared for next detection event, simply by turning the laser off for short period of time (assuming that additional binding sites are available for a subsequent detection event).

Table 2 below illustrates a comparison of the sensitivity of a preferred embodiment of the present invention to a conventional microcavity-sensing approach without non-linearity (Vollmer, F., D. Braun, et al., "Protein detection by optical shift of a resonant microcavity," *Applied Physics Letters* 80(21): 3 (2002); Arnold, S., M. Khoshsima, et al., "Shift of whispering-gallery modes in microspheres by protein adsorption," *Optics Letters* 28(4): 272-274 (2003)).

TABLE 2

| Vertical distance to the center of the cavity (nm) | Minimal detectable particle radius(nm) |
|---|---|
| 400 | 60 |
| 110 (right on top of the cavity) | 20 |
| 0 (center of the cavity) | 14 |

| Fluctuation (in detuning) | Fluctuation (in power) | Detectability (in radius nm) |
|---|---|---|
| $\Delta\delta = 0.1$ | 10%(0.05 dB) | 7-10 |
| $\Delta\delta = 0.01$ | 1%(0.004 dB) | 3-5 |
| $\Delta\delta = 0.001$ | 0.1%(0.0004) | 1.3-2 |

As mentioned above, the conventional sensing scheme depends on the ability to detect small shifts in the cavity resonance due to the presence of the analyte. These shifts need to be on the order of the cavity linewidth $\gamma_0$ ($\gamma_0=\omega_0/Q$, $\omega_0$ is the cavity resonance frequency) in order to be detected. Although we have shown that 1/50 of cavity linewidth can be detected, this method is fundamentally spectrally limited. In contrast, in the presence of optical bistablity, the transmission exhibits a sharp, instant drop at the infinitesimal red detuning of the nonlinear resonance. Since the nonlinear resonance depends on the input power, this detection scheme requires a stable laser source. The sensitivity of the proposed scheme depends on its initial state. The less detuned the cavity is from the laser light in the initial state A (FIG. 5B), the more sensitive the system. However, this also makes system more susceptible to the noise, and therefore the ultimate sensitivity is determined by the noise of the instrumentation.

Table 2(top) shows the sensitivity of conventional spectroscopy scheme (with Q=100,000), assuming here that the induced wavelength shift due to analyte must be on the order of the linewidth for detection. In the digital sensing scheme (Table 2 (bottom)), the detection sensitivity is determined by how stable the input state is. The initial state A in FIG. 5B can be initialized as close to the unstable point, as long as all the noises/fluctuations in the input signal is not high enough to trigger the digital jump. These perturbations from signal or noise can be expressed as a change in the detuning, termed as $\Delta\delta$ in Table 2(top). The major noise is power fluctuation in the input laser. Although the laser wavelength is stable typically within 0.02 μm over minute-timescales, the input power will vary so that $\Delta\delta\sim0.1$ Table 2(bottom) shows that in order to detect a molecule of size 1 nm range, the power has to be stable within 0.1% assuming the cavity has Q=100,000, and the particle is on top of the nanobeam cavity.

Figure 2A:
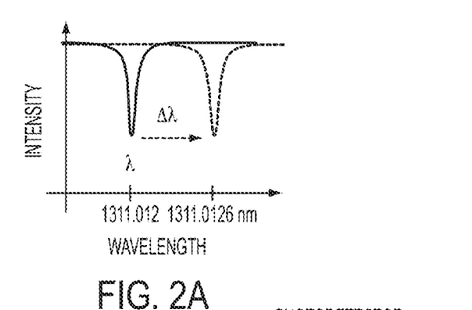
FIG. 2A is a graph of resonance wavelength shift $\Delta\lambda$.
Figure 2B:
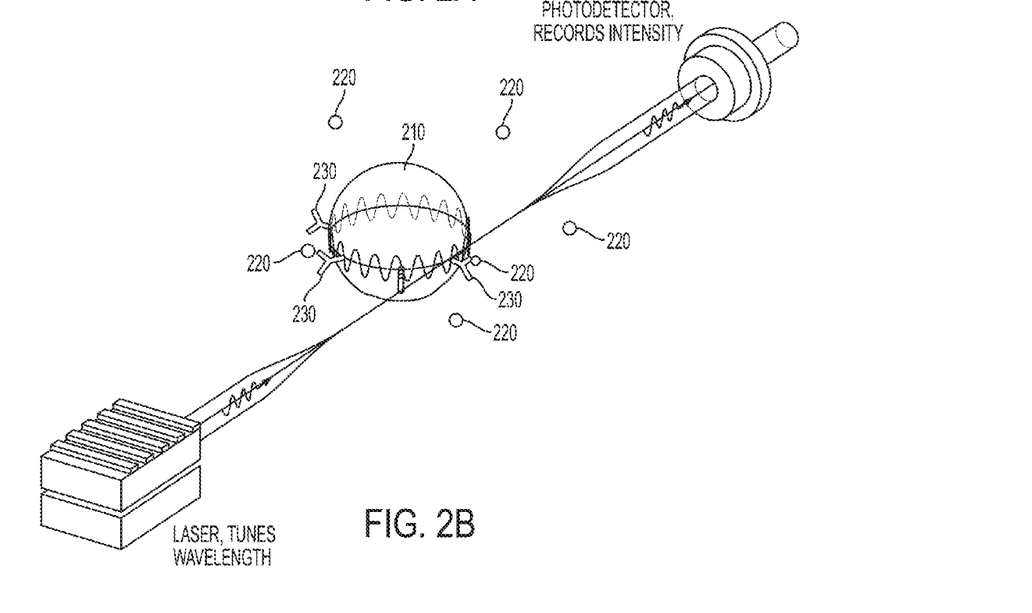
FIG. 2B is a diagram illustrating the binding of molecules 220 to a microbead resonator 210, and functionalized with antibodies 230. Resonance is identified from a minimum recorded in the fiber-transmission spectrum as the laser wavelength is tuned across the resonance wavelength of the microbead.
Figure 2C:
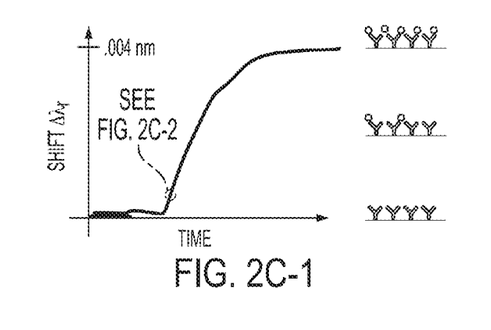
Figure 2C:
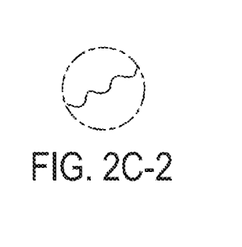
Figure 7A:
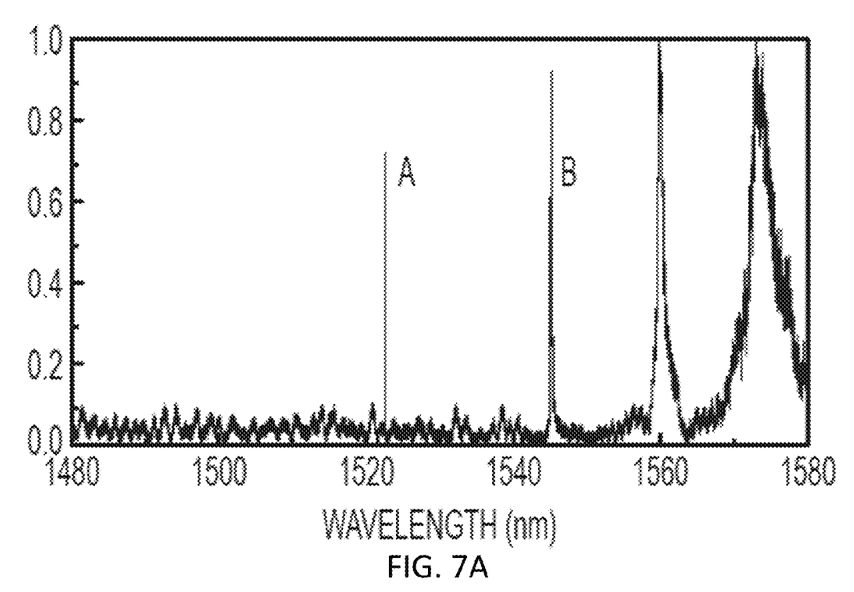
FIG. 7A is a graph showing preliminary data of a transmission spectrum for a fabricated device measured at 100 microwatts input power. Sharp cavity resonances (A and B) with very narrow linewidth can be observed.
Figure 7B:
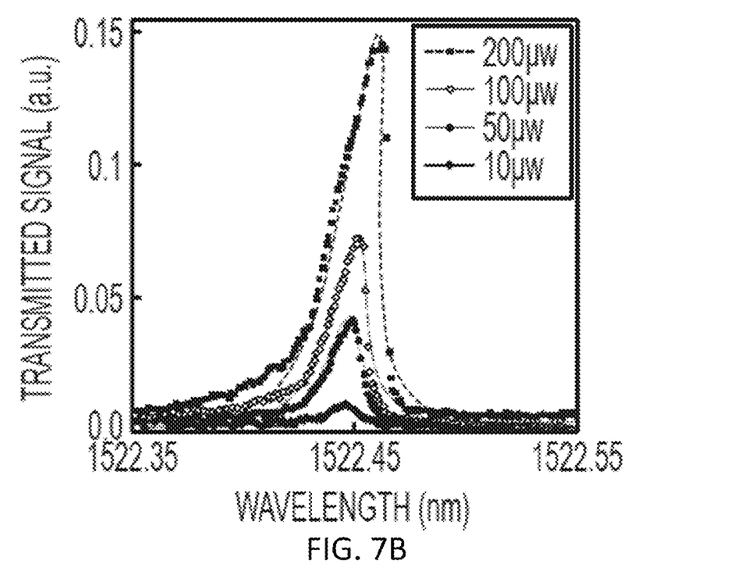
FIG. 7B is a zoom in of mode A in 4 at different input power levels.
Figure 8:
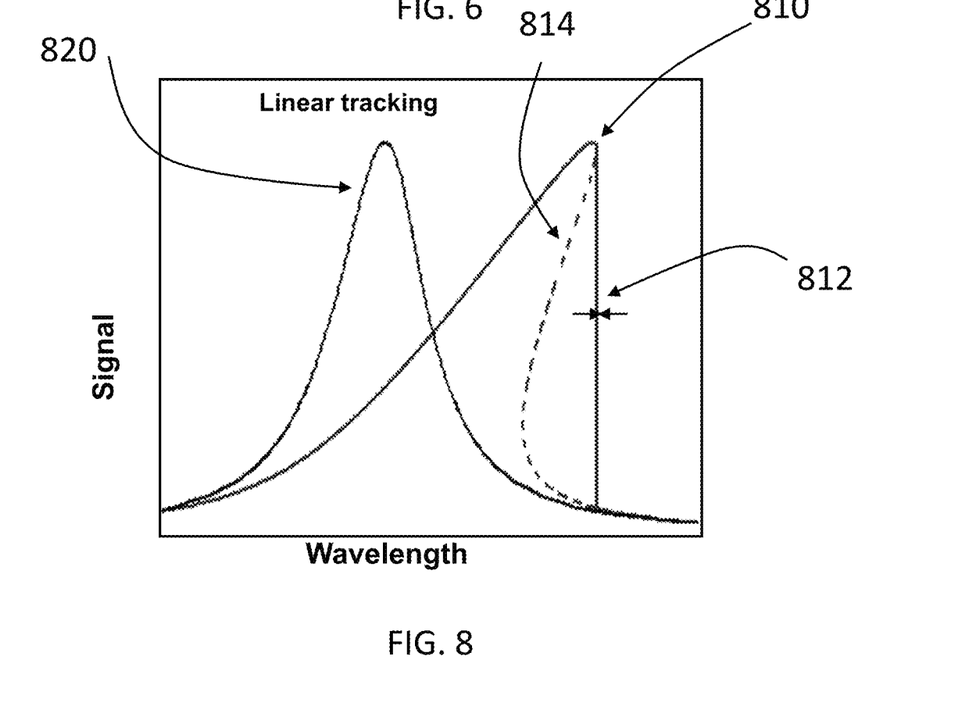
FIG. 8 is a graph comparing a conventional linear tracking method 820 and the BCS tracking method 830. The sharp drop in power at the edge of the bistable region 812 serves as an ideal tracking feature for monitoring small shifts induced by analyte.

Bistable Cavity Sensing (BCS) for Quantitative Analysis of Biomarker Concentration As in the conventional sensing approach, illustrated in FIG. 2A, the sensitivity of the method is limited by the smallest shift in the cavity resonance that can be detected, which in turn is limited by the linewidth of the resonance. In the proposed BCS method, effective linewidth of the resonance can be significantly reduced (Experiment FIG. 7B, schematic FIG. 8 (curve 820 820)) due to the effects of optical bistability: the spectrum shows a sharp drop in the transmitted power at the edge of the bistable region, with an effective width limited only by the frequency resolution and stability of the laser, and therefore serves as an ideal tracking feature for monitoring small shifts induced by analytes. The mechanism of BCS method works as following: as the wavelength of the laser source approaches the cavity resonance, optical energy builds up inside the cavity. A portion of the energy is converted into heat, inducing a change in the refractive index of silicon. This power dependent refractive index produces a bistable region in the cavity transmission spectrum (shown as dashed line 814 in FIG. 8). As a result, sweeping the wavelength of the input laser in an increasing manner across the cavity resonance causes the cavity to operate at one stable state, right up until the laser wavelength reaches the bifurcation point at the long-wavelength end of the bistable region (shown as solid line 810 in FIG. 8). At this wavelength, energy is released from the cavity and the cavity transmission drops discontinuously to the low-transmission state. Our sensor operates by monitoring analyte-induced shifts in the wavelength at which this output signal discontinuity occurs. Importantly, the wavelength uncertainty of this drop has a sharpness limited only by the wavelength resolution and stability of the laser, and is independent of the cavity Q-factor. In addition, the transmission drop can be orders of magnitude larger than the noise level of the system (detector in particular), resulting in high the signal-to-noise ratio (SNR) in our system.

Figure 4:
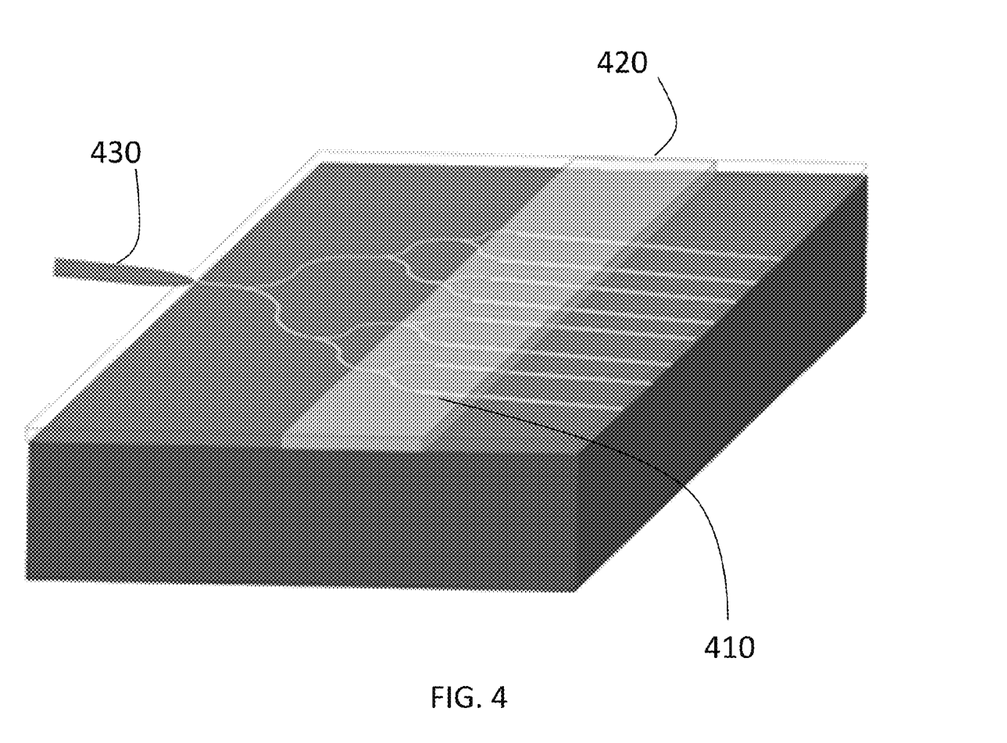
FIG. 4 is a diagram of an example of alternative configuration of sensing platform.

Photonic Crystal Nanobeam Cavities for Non-Linear Biochemical Sensing Applications In order to demonstrate compact, highly-integrable, on-chip bio-sensors discussed above, nanobeam cavities were designed in order to optimize their performance. A photonic crystal (PhC) nanobeam cavity structure 400 of the present invention is shown in FIG. 4. It consists of a silicon ridge waveguide 410 with designed nano-holes 420 patterned along the waveguide 410. The holes 420 are largest in the center of the cavity 410 and tapered monotonically to both ends, where the cavity 400 is connected to the feeding optical waveguide. Such nanostructures may be designed deterministically to have simultaneously high quality factor Q and high transmission to the feeding silicon waveguide (used to bring light to the cavities). A preferred embodiment of the present invention is shown in FIG. 3. The device 300 is fabricated in a silicon-on-insulator (SOI) material platform (220 nm thick Si device layer 302 on top of 2,000 thick $SiO_2$ 304) using previously developed recipes. E-beam lithography, followed by reactive ion etching, may be used to fabricate devices in Si device layer 302. Next, couplers 310 (2 μm×2 μm polymer pads, n=1.58) are defined on top of waveguides to facilitate in- and out-coupling from an optical fiber 320. Finally, the devices are capped with Teflon layer (CYTOP) which makes them mechanically and chemically robust. CYTOP, non-fouling, microfluidic channels 330 are built on top of optical resonators or cavities 400 to facilitate the delivery of analyte 340 (perfluoropolymers like CYTOP are known to exhibit very little unspecific adsorption of biomolecules). The CYTOP polymer will be thinned or completely removed at the microcavity region to enhance interaction between cavity optical fields with proximal biomolecules (analyte).

The geometry can support very sharp optical resonances (FIG. 6.1). Blow-up of cavity resonances indicate non-symmetric (non-Lorentzian) shape (FIG. 6.1b) indicative of nonlinear, bi-stable, response of our devices, even at ultra-low input powers (~tens of microwatts). An optical bistablity equation (Soljacic, Luo et al. 2003; Bravo-Abad, Rodriguez et al. 2007) was used to fit FIG. 7B to extract quality factors of the cavities. Preliminary devices are estimated to have quality factors of 80,000 with 73% on-resonance transmission. Also, immersion in a liquid solution did not significantly degrade the Q.

The sensing paradigm to be pursued in the proposed program will capitalize on this bistable response of our devices. One can further optimize our photonic crystal nanobeam cavity with the goal of achieving high Q and nonlinear bistablity at ultra-low power levels. One can also explore the use of a tapered input fiber that will be glued to the polymer pad to make the device more robust and more convenient to characterize. Furthermore, one can explore the possibility of replacing electron beam lithography with deep UV photolithography as well as imprint lithography for potential inexpensive mass production.

Chemical Modification of Nanobeam Cavities with DNA Recognition Elements and Practical Demonstration of Biosensing Methods in accordance with the present invention modify the exposed surface of nanobeam cavities with DNA biorecognition elements. One can quantitate signal-readout after exposure of the nanobeam resonators to varying concentrations of DNA target analyte using our established theory for the dispersive and optically-bistable shift of the wavelength; and characterize sensor performance in dose-response curves. The nanobeam sensor is operated in the low power regime without effects of non-linearity, as well as in the higher-power regime to enable optical bistability. The functionalized nanobeam cavities of the present invention may be used to demonstrate digital biosensing with a specific DNA target molecule.

Figure 9:
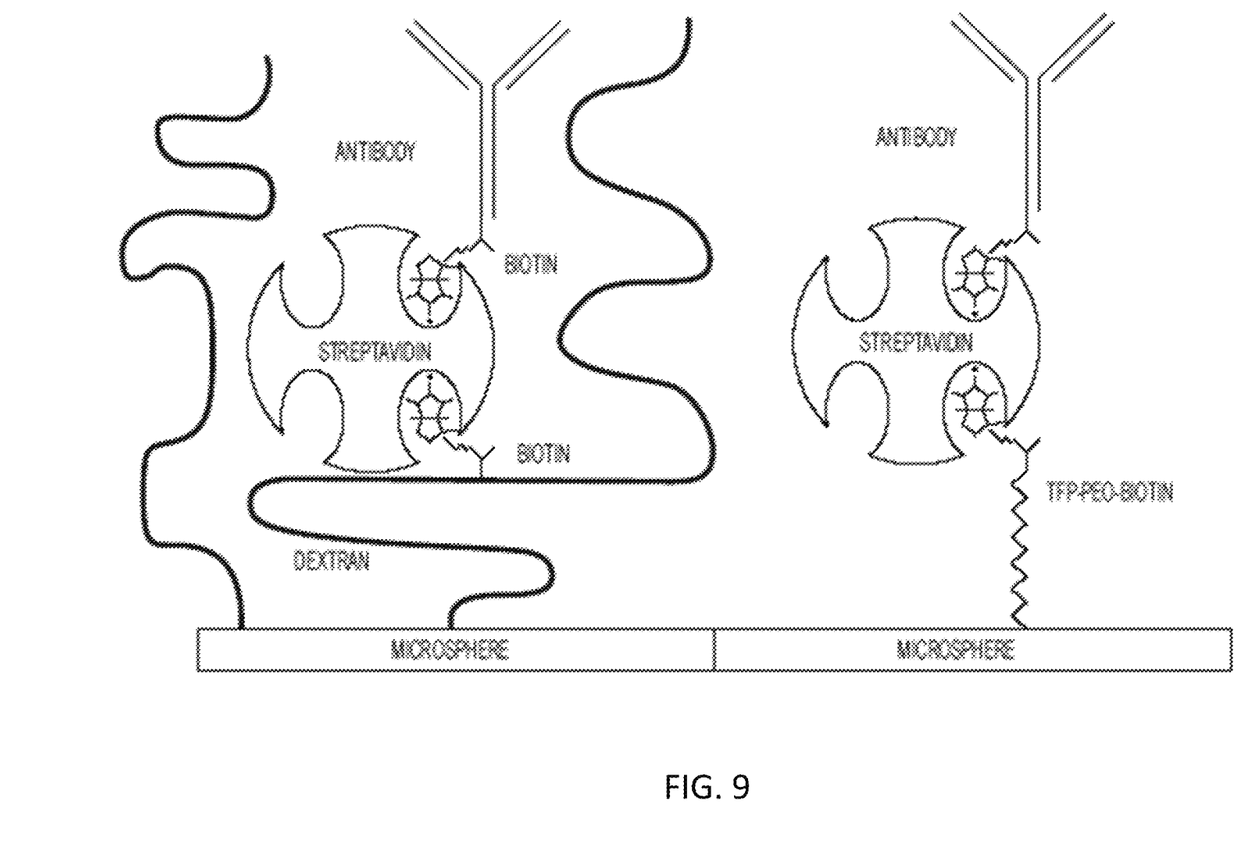
FIG. 9 illustrates examples for two strategies to conjugate biotinylated antibody or DNA oligonucelotides onto silica substrate using biotinylated dextran hydrogel (left) or TFP-PEO biotin (right) linkers.

One can conjugate olignucleotides on nanobeams and validate their biosensing capability. Several surface chemistries are used to conjugate oligonucleotides to the surface of nanobeam photonic crystal cavities. In the first approach, biotinylated dextran polymer is adsorbed to the terminal silica nanobeam surface (FIG. 9). The use of a biotin-dextran polymer has the advantage that it will maximize the effective surface density of immobilized streptavidin molecules immobilized throughout the 3D dextran hydrogel. We then link from the immobilized streptavidin proteins to biotinylated oligonucleotides. In the second approach, tetraphenyl-ester (TFP) polyethylene oxide (PEO) biotin is used to modify silica nanobeam surface (FIG. 9). TFP reacts with primary amines which we introduce on our silica nanobeam surface through vapor-phase aminosilanization. We then couple the TFP-PEO biotin via streptaviding to the biotinylated oligonucleotide. In a third approach, a high pH carbonate (or other) coating buffer is used. The oligonucletoides (coupled to streptavidin) are diluted in the buffer and coat on the nanobeams for a few hours or overnight.

Figure 10:
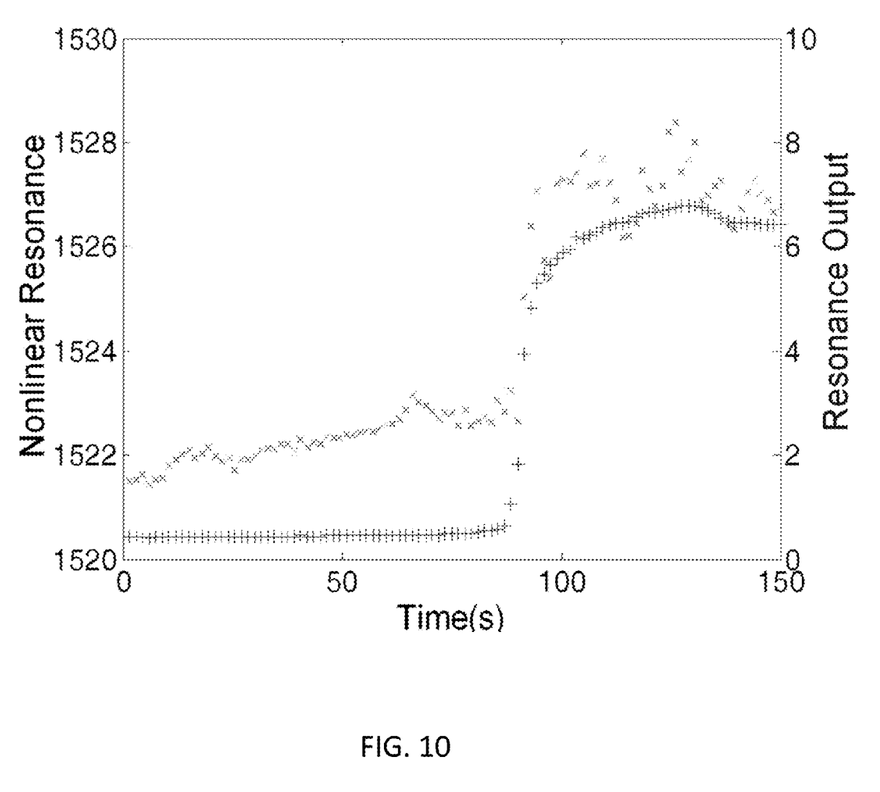
FIG. 10 is a graph of nanobeam biosensor response to adsorption of dextran hydrogel. "+" indicates the shift in resonance wavelength, "x" indicates a change in the amplitude of the resonant line.

The biosensing technique at low coupling power (so that the effects of nonlinearity can be ignored) may be used to monitor changes in resonance wavelength as molecules bind to the nanobeam surface. From the wavelength shift signal we quantitate the amount of surface immobilized dextran, streptavidin as well as oligonucleotide molecules. The nanobeam-waveguide setup is mounted on an upright microscope for convenient inspection of the surface modification procedure and to ensure that the nanobeams are properly exposed to various solvents and solutions. Exposure to different chemical solutions is achieved by dispensing small droplets directly on the nanobeam cavity, using a conventional or Pasteur pipette. In another approach, obotic spotting machines are used for this purpose. And in yet another approach, we use perfluoropolymer CYTOP to pattern microfluidic channels for delivery of various solutions, where a glass slide (possibly further coated with adhesive polymer) is used to seal the fluidic microchip. An automated approach based on robotic spotters to facilitate modification of larger nanobeam sensor arrays with different oligonucleotides also may be used, for example in gene chip applications that use libraries of sequence tags (ESTs) or other sources of oligonucleotides for genomic detection. Preliminary data for the predictive wavelength shift signal of a nanobeam biosensor (operated in the low power regime) in response to adsorption of dextran hydrogel from a solution in distilled water is shown in FIG. 10. The quantitative data (not further analyzed here) suggests that tracking the wavelength shift signal will be ideal to quantitate and optimize surface modification procedures.

Similar binding curves may be acquired to optimizing the functionalization with dextran, streptavidin and oligonucleotides. The nanobeam arrays are designed so that they are separated by a large enough distance so that we can perform the surface functionalization for each nanobeam separately by using simple pipettes to deliver specific solutions or by using previously developed integrated microfluidics. Robotic spotting techniques may be used for this purpose, which may allow one to reduce the nanobeam separation in array format, possibly to less than 100 µm since the minimal spot size of a robotic spotter is on the order of 10 µm. A bulk quantity of nanobeam arrays modified with different oligonucleotides (for example 2-10 different random 11-mer sequences) may be produced and stored in the dry state. Judging from preliminary experiments the surface coating of dried nanobeams is estimated to be stable for at least a couple of months.

High-Throughput DNA Biomarkers Detection with Nanobeam

Fabrication may be scaled-up to realize nanobeam sensors in array format. Geometrical parameters (cavity spacing, location on a chip, integration with waveguides) are established which allow for effective surface functionalization and effective optical readout of nanobeam arrays (see FIG. 3). Several nanobeams are modified with different oligonucleotide recognition elements, using manual (pipette-based) or robotic (spotter-base) surface modification procedures, as well as microfluidic approaches. For this, the nanobeams are encapsulated in CYTOP layer, which are opened-up only in selective regions using reactive ion etching to fully expose the top surface of the nanobeam and to pattern microfluidic channels. Each nanobeam surface is then modified by either printing small drops of fluid directly on sensor elements using robotic spotters or by using other printing techniques, for example dip-pen lithography, ink-jet printing, gene-chip spotters, BioNanoforce Inc. droplet dispensers etc. A sensor array is modified with several oligonucleotide recognition elements, possible obtained from a DNA library (expressed sequence tags (ESTs) or other), and then is exposed to a sample that contains all of the respective complementary target sequences. After exposure to the target sample, we attempt multiplexed threshold-level detection of DNA hybridization in parallel. For this, we optimize the length of the oligonucleotide recognition element, the salt concentration of the hybridization buffer, and the optimal detuning from cavity resonance to realize threshold-level detection at relevant target DNA concentrations (µM-pM) and affinities (7-20 mers). We also investigate protocols to reset cavities after a first detection event so that one can prime the device for a second (and many subsequent) sensing events. This requires an experimental setup where one does not detect equilibrium binding, but rather the rate constant for binding of a target molecule (or a certain number of target molecules). We implement a scheme where we will detune the cavity so that a fixed number of molecules, possibly down to one molecule, will tune the cavity on resonance after binding. Then we reset to an adjusted initial condition so that this discrete detection event can be repeated several times until all binding sites are saturated or until equilibrium conditions have been established. From this data we extract rate constants, affinity constants, and concentration of target analyte. By varying experimental conditions such as temperature, buffer composition etc. we extract thermodynamic parameters related to DNA hybridization.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment was chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What we claim is:

1. An optical device comprising:
a laser source;
input waveguides connected to said laser;
a material structured on a micro-nanoscale to localize light in a modal volume where constructive interference produces optical resonance, wherein said material exhibits third-order nonlinearity and is modified with molecular recognition elements immobilized within some part of the optical field, said material being connected to said input waveguides;
output waveguides connected to said material; and
a photo-detector connected to said output waveguides;
wherein said material is exposed on one or more sides to a liquid sample in a sample volume, and
wherein a geometry of said material structured on the micro- or nanoscale is selected from a high quality factor (Q) photonic crystal defect cavity, a high quality factor (Q) photonic crystal nanobeam cavity, and a high quality factor (Q) photonic crystal.

2. An optical device according to claim 1, where the geometry of the micro- or nanoscale structure is a geometry that produces an optical microcavity structure comprising at least one micro-cavity.

3. An optical device according to claim 1, wherein said material comprises one of the following: silicon, silica, silicon nitrate, diamond, doped glass, high-index glass, quartz, polymer, polydimethylsiloxane, InP, and materials.

4. An optical device according to claim 1, Wherein said non-linearity of said material originates from heating of said material b two-photon and/or free carrier absorption.

5. An optical device according to claim 1, wherein said non-linearity of said material originates from at least one of the following: second order nonlinearity, optomechanically induced nonlinearity, and Kerr nonlinearity.

6. An optical device according to claim 1, where a resonant frequency of said device is in the visible, in the near-infrared, in the mid-infrared or in the UV.

7. An optical device according to claim 2, wherein a resonance frequency of each micro-cavity can be reconfigured mechanically, by heating, by carrier injection, or by nonlinear optical processes.

8. An optical device according to claim 2, where each micro-cavity is individually excited, or simultaneously excited, where each micro-cavity is excited using optical fibers, tapered optical fibers, or through focused or non-focused optical beams.

9. An optical device according to claim 2, wherein a signal from each micro-cavity is transferred to optical waveguides, arrays of optical fibers, imaging arrays, or detector arrays.

10. An optical device according to claim 1 wherein the sample volume comprises a microfluidic channel, an open reservoir, or a capillary.

11. A method for detection of biomolecular targets comprising the steps of:
coupling of light to the device according to claim 1 at an optical frequency that is slightly blue-detuned from the resonance frequency;
detecting transmitted power with the photodetector;
exposing the molecular recognition elements to target molecules dissolved in the liquid sample;
recording a discrete change of transmitted power in response to specific binding of target molecules to the recognition elements;
recording a power versus time trace on a computer; and
resetting the device by blue-detuning so that the new frequency is blue-detuned to the new resonance frequency of the device according to claim 1.

12. An optical device according to claim 1, wherein the geometry of the micro- or nanoscale structure is a geometry that produces an optical cavity structure comprising a plurality of nano- or micro-cavities; and wherein the plurality of nano- or micro-cavities are multiplexed in array or matrix format on a chip substrate.

13. An optical device according to claim 1 wherein molecular recognition elements comprise one of the following: DNA, single stranded DNA, proteins, antibodies, dendrimers, nanostructures, bacterial S proteins, lectins, glycoproteins, membranes, membrane components, lipid bilayers, and organelles.

14. A method of analyzing the concentration, binding kinetics and affinity of biomolecular targets comprising the steps of:
coupling of light to the device according to claim 1 at various optical frequencies;
detecting a transmitted power with said photodetector at each frequency; and
analyzing a resonance obtained by the photodetector.

15. A method to accommodate for varying receptor affinity by blue detuning of the resonance frequency to a certain wavelength so that a certain number of molecules will trigger a discrete change in transmitted optical power.

16. The optical device according to claim 1 wherein the high quality factor (Q) is at least about $10^5$.

* * * * *